(12) United States Patent
Morris et al.

(10) Patent No.: US 8,513,601 B2
(45) Date of Patent: *Aug. 20, 2013

(54) SYSTEMS FOR DETECTING CHARGED PARTICLES IN OBJECT INSPECTION

(75) Inventors: Christopher L. Morris, Los Alamos, NM (US); Mark F. Makela, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/591,118

(22) Filed: Aug. 21, 2012

(65) Prior Publication Data

US 2012/0312985 A1    Dec. 13, 2012

Related U.S. Application Data

(63) Continuation of application No. 12/447,459, filed as application No. PCT/US2007/082735 on Oct. 26, 2007, now Pat. No. 8,247,767.

(60) Provisional application No. 60/855,064, filed on Oct. 27, 2006.

(51) Int. Cl.
*G01N 23/00* (2006.01)

(52) U.S. Cl.
USPC .................................................. 250/307

(58) Field of Classification Search
USPC ........................................... 250/307
See application file for complete search history.

(56) References Cited

PUBLICATIONS

Bychkov et al., "The large size straw drift chambers of the COMPASS experiment," 2006, Nuclear Instruments and Methods in Physics Research A, vol. 556, pp. 66-79.*

* cited by examiner

*Primary Examiner* — Kiho Kim
(74) *Attorney, Agent, or Firm* — Perkins Coie LLP

(57) ABSTRACT

Techniques, apparatus and systems for detecting particles such as muons. In one implementation, a monitoring system has a cosmic ray-produced charged particle tracker with a plurality of drift cells. The drift cells, which can be for example aluminum drift tubes, can be arranged at least above and below a volume to be scanned to thereby track incoming and outgoing charged particles, such as cosmic ray-produced muons, while also detecting gamma rays. The system can selectively detect devices or materials, such as iron, lead, gold and/or tungsten, occupying the volume from multiple scattering of the charged particles passing through the volume and can also detect any radioactive sources occupying the volume from gamma rays emitted therefrom. If necessary, the drift tubes can be sealed to eliminate the need for a gas handling system. The system can be employed to inspect occupied vehicles at border crossings for nuclear threat objects.

14 Claims, 12 Drawing Sheets

| MATERIAL | dE/dx | $\chi$ |
|---|---|---|
| | MeV-cm$^2$/gm | cm |
| H$_2$O | 2.06 | 36 |
| Fe | 1.87 | 1.76 |
| Pb | 1.54 | 0.56 |

FIG. 10

SYSTEMS FOR DETECTING CHARGED PARTICLES IN OBJECT INSPECTION

PRIORITY CLAIMS AND RELATED APPLICATIONS

This patent application is a continuation of U.S. patent application Ser. No. 12/447,459, filed on Oct. 26, 2009 now U.S. Pat. No. 8,247,767, which is a U.S. National Stage Application under 35 U.S.C. §371 of International Patent Application No. PCT/US2007/082735, filed on Oct. 26, 2007, which claims benefit of priority of U.S. patent application Ser. No. 11/771,169, filed on Jun. 29, 2007, now U.S. Pat. No. 7,633,062, which claims benefit of priority of U.S. Provisional Patent Application No. 60/855,064, filed on Oct. 27, 2006.

The disclosures of the above patent applications are incorporated herein by reference.

STATEMENT REGARDING FEDERAL RIGHTS

This invention was made with Government support under Contract Number DE-AC52-06NA25396 awarded by the United States Department of Energy. The Government has certain rights in the invention.

TECHNICAL FIELD

Embodiments relate to fields of particle detection, analysis, control and, more particularly but not exclusively, to security and portal monitoring systems and methods.

BACKGROUND

The threat of the detonation of a nuclear device in a major US city has prompted research aimed at providing more robust border surveillance for contraband nuclear material.

An article entitled "A Terrorist Threat—The movement of Black Market Nuclear Materials into the United States" dated November 2001 in the name of Gene R. Kelley from the article archives of the Nuclear Age Peace Foundation, PMB 121, 1187 Coast Village Road, Suite 1, Santa Barbara, Calif. 93108, USA, outlines the problem of surreptitious transport of special nuclear material. Kelly refers to some possibilities for moving this type of material as being as follows:

1)—superimpose the shipment of small, well-shielded packages on established drug and contraband routes.

2)—ship materials conventionally in well shielded, small containers through a surreptitiously network of widely dispersed handlers.

3)—man carrying many small quantities across the mostly porous borders of the United States.

4)—use diversified distribution techniques (routes and conveyances) by requiring multiple way-points and altering the characteristics of external shipping containers at each point.

5)—mix materials and legitimate products for routine deliveries.

Kelley concludes that the formidable nature of the tasks required to detect and identify well packaged fissile materials renders the likelihood of detection in small quantities highly questionable.

The use of portal monitors at border crossing points is becoming routine for detecting smuggled nuclear materials. In many cases shielding can be used to obscure a nuclear signature. Conventional nuclear material detectors use high resolution gamma or X ray detectors.

Unshielded Kg quantities of highly enriched uranium can be detected with high reliability with 1 minute counting times by detecting gamma rays from the 238U impurity. FIG. 1 of the accompanying drawings depicts example count data from a high resolution gamma ray detector used to detect Weapon grade uranium (WGU): 10% 238U 90% 235U without shielding and with 5 cm and 2.5 cm of lead shielding, respectively. FIG. 1 indicates how self-shielding of nuclear material reduces count rates. In order to shield a threat object, about 5 cm thick lead, gold, tungsten, or other shielding material is required.

As indicated by FIG. 1 and additionally FIGS. 2 and 3, which illustrate simulations of X-radiography of 20 kg of uranium among automobile differentials using a fan beam of x-rays generated by 8 MV electron bhemstralung source. These simulations show that X-ray radiography can visualize objects, even in some dense, cluttered cargo, but definitive signatures of high z objects are confused by scatter backgrounds and transmission is insufficient for many cargos.

Having regard to the foregoing, the small amount of material needed to construct a nuclear device and the ease with which neutron and gamma ray signatures can be obscured with shielding makes robust border surveillance for contraband nuclear material difficult.

BRIEF SUMMARY

The following summary of the invention is provided to facilitate an understanding of technical features related to techniques, apparatus and systems for detecting particles such as muons and is not intended to be a full description. A full appreciation of the various aspects of the invention can be gained by taking the entire specification, claims, drawings, and abstract as a whole.

Techniques, apparatus and systems for detecting particles such as muons are described in various examples. In one implementation, a particle detection system is described to include a first set of position sensitive charged particle detectors located on a first side of an object holding area to measure positions and directions of incident charged particles towards the object holding area, a second set of position sensitive charged particle detectors located on a second side of the object holding area opposite to the first side to measure positions and directions of outgoing charged particles exiting the object holding area, and a signal processing unit, which may include, e.g., a microprocessor, to receive data of measured signals of the incoming charged particles from the first set of position sensitive charged particle detectors and measured signals of the outgoing charged particles from the second set of position sensitive charged particle detectors. This signal processing unit is configured to analyze scattering of the muons in the materials within the object holding area based on the measured incoming and outgoing positions and directions of charged particles to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive charged particle detector can be implemented in various configurations, including drift cells such as drift tubes filled with a gas which can be ionized by charged particles. The drift cells can be arranged to allow at least three charged particle positional measurements in a first direction and at least three charged particle positional measurements in a second direction different from said first direction. The drift cells can be further adapted and arranged on surrounding sides of the volume such that the drift cells form a box or four sided structure. Such a system can be used to utilize natural cosmic ray-produced muons as the source of muons for detecting one or more objects in the object holding area. For example, the system can be employed to inspect occupied vehicles at border crossings for nuclear threat objects.

The aforementioned aspects of the invention and one or more advantages can now be achieved as described herein.

According to one aspect, a monitoring system has a cosmic ray-produced charged particle tracker with a plurality of charged particle detectors. The charged particle detectors are in the form of drift cells, which can be for example drift tubes of circular or non-circular cross section or non-tube shaped cells, configured both to enable tracking of incoming and outgoing charged particles passing through a volume to be scanned, such as cosmic ray-produced muons, and detection of gamma rays. The system can both selectively detect devices or materials, particularly but not exclusively high density materials such as iron, lead, gold and/or tungsten, occupying the volume from multiple scattering of the charged particles passing through the volume and detect radioactive sources occupying the volume from gamma rays emitted therefrom.

Advantageously, adopting drift cells as charged particle detectors in the cosmic ray tracker effectively provides the combined function of a cosmic ray radiography apparatus with a gamma radiation counter to provide a robust detector for nuclear threats. This eliminates the need for two separate instruments.

The drift cells can be sealed drift cells further reducing the cost and complexity of the system by eliminating the need for a gas handling system.

A typical operating gas of the drift tubes comprises a non-flammable gas, such as a mixture of argon, carbon dioxide and Tetrafluoromethane ($CF_4$)

The drift cells can comprise a set of drift tubes located above the volume and another set of drift tubes located below the volume. Each set of drift tubes can have at least three drift tubes configured in a first direction and another at least three drift tubes configured in a second direction. The first direction can be orthogonal to the second direction.

A gamma ray or neutron source can be arranged within the system to enable active interrogation of material occupying the volume.

According to another aspect, a monitoring system has a cosmic muon tracker having a plurality of muon detectors in the form drift cells. The drift tubes can be arranged at least above and below a volume to be scanned both to enable tracking of incoming and outgoing muons and counting of gamma rays. In use, the system can both selectively detect high density shielding of radioactive material occupying the volume from multiple scattering of the muons passing through the volume and detect the radioactive material occupying the volume from gamma rays emitted therefrom.

The volume to be scanned can be of sufficient size to enable a vehicle or cargo container to occupy the volume. Advantageously, adopting drift tubes as muon detectors enables the system to perform passive scanning of occupied passenger vehicles with short scanning times and no dose radiation above ambient background.

According to yet another aspect, a method of monitoring comprises arranging a plurality drift cells on opposite sides of a volume to be scanned; detecting with the drift cells incoming and outgoing cosmic ray-produced charged particles together with any gamma rays; selectively detecting any material occupying the volume from multiple scattering of the charged particles passing through the volume; and detecting from the gamma rays any radioactive sources occupying the volume.

Arranging the plurality of drift cells can comprise arranging a set of at least three planes of drift tubes above the volume and arranging a set of at least three planes of drift tubes below the volume and can further comprise arranging the drift tubes in each plane in two orthogonal coordinates.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIGS. 2 and 3, 1 (Prior Art) illustrate X-ray radiography simulations of uranium detection among automobile differentials and a fan beam 8MV;

FIG. 10 depicts a table showing theoretical energy loss rate (dE/dx) and radiation length (X) for various material.

DETAILED DESCRIPTION

Figure 1:
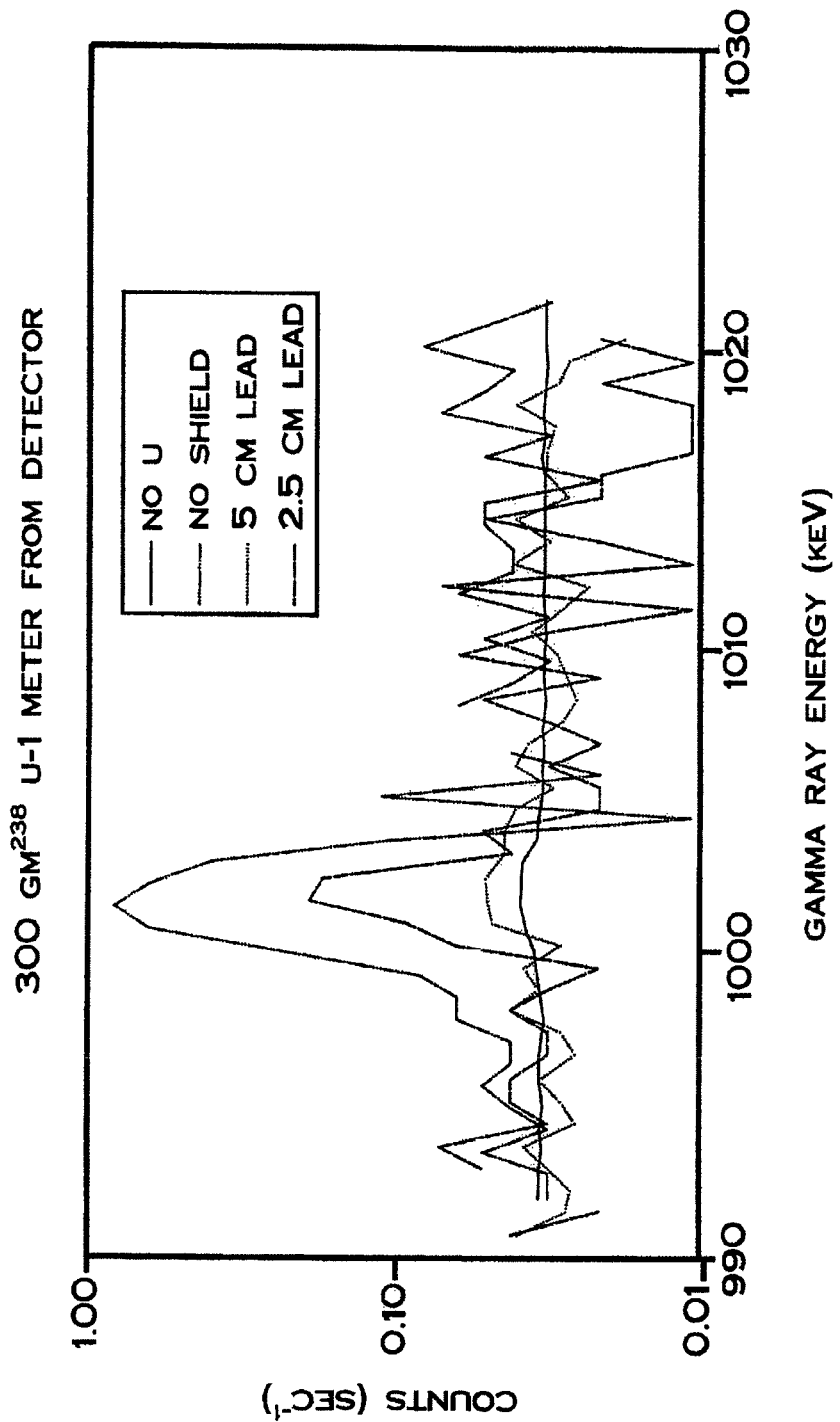
FIG. 1 illustrates example count data from a high resolution gamma ray detector used to detect Weapon grade uranium (WGU): 10% 238U 90% 235U, using the gamma-ray signal from a 400 gm sample of 238U, without shielding and with 5 cm and 2.5 cm of lead shielding, respectively.
Figure 2:
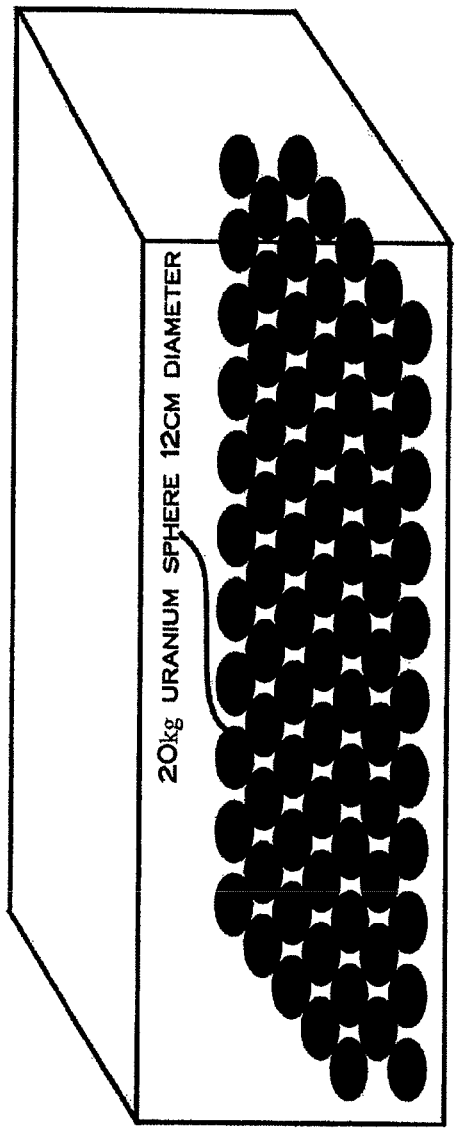
Figure 3:
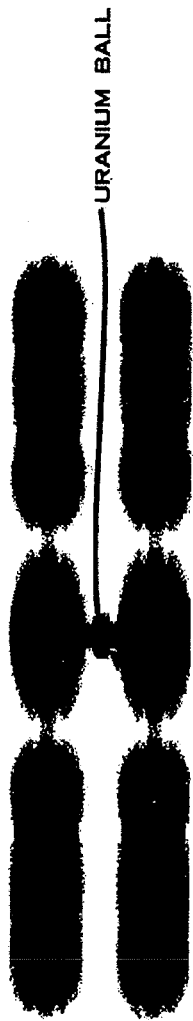

The particular values and configurations discussed in these non-limiting examples can be varied and are cited merely to illustrate at least one embodiment of the present invention and are not intended to limit the scope of the invention.

The particle detection systems and methods described in this application can be implemented to detect presence of certain objects or materials such as nuclear materials and to obtain tomographic information of such objects in various applications including but not limited to inspecting packages, containers, occupied vehicles at security check points, border crossings and other locations for nuclear threat objects that may range from fully assembled nuclear weapons to small quantities of highly shielded nuclear materials. Features described in this application can be used to construct various particle detection systems.

For example, a particle detection system can include an object holding area for placing an object to be inspected, a first set of position sensitive muon detectors located on a first side of the object holding area to measure positions and directions of incident muons towards the object holding area, a second set of position sensitive muon detectors located on a second side of the object holding area opposite to the first side to measure positions and directions of outgoing muons exiting the object holding area, and a signal processing unit, which may include, e.g., a microprocessor, to receive data of measured signals of the incoming muons from the first set of position sensitive muon detectors and measured signals of the outgoing muons from the second set of position sensitive muon detectors. As an example, each of the first and second sets of particle detectors can be implemented to include drift tubes arranged to allow at least three charged particle positional measurements in a first direction and at least three charged particle positional measurements in a second direction different from the first direction. The signal processing unit is configured to analyze scattering behaviors of the muons caused by scattering of the muons in the materials within the object holding area based on the measured incoming and outgoing positions and directions of muons to obtain a tomographic profile or the spatial distribution of scattering centers within the object holding area. The obtained tomographic profile or the spatial distribution of scattering centers can be used to reveal the presence or absence of one or more objects in the object holding area such as materials with high atomic numbers including nuclear materials or devices. Each position sensitive muon detector can be implemented in various configurations, including drift cells such as drift tubes filled with a gas which can be ionized by muons. Such a system can be used to utilize natural cosmic ray-produced muons as the source of muons for detecting one or more objects in the object holding area.

As will be explained in more detail below, in particular illustrative embodiments, the particle detection systems can utilize drift tubes to enable tracking of charged particles, such as muons, passing through a volume as well as concurrent detection of neutron particles. However, those skilled in the art would understand that such charge particle detectors can be employed in applications other than cosmic ray-produced charged particle tracking to detect charged particles other than cosmic ray-produced charged particles. These charged particle detectors are applicable to any charged particle from any appropriate source. For example, muons can be produced by cosmic rays or a low intensity beam of muons from an accelerator.

In applications for portal monitoring, the illustrative embodiments provide an approach to enable robust nuclear material detection at reduced cost and with increased effectiveness. Furthermore, the approach can provide a radiation portal monitor which is capable of determining if a given vehicle or cargo is free of nuclear threats by both measuring the absence of a potential shielded package and the absence of a radiation signature.

The portal monitoring systems of the illustrative embodiments shown in the accompanying drawings employ cosmic ray-produced charged particle tracking with drift tubes. As will be explained in more detail below, the portal monitoring systems utilize drift tubes to enable tracking of charged particles, such as muons, passing through a volume as well as detection of gamma rays. Advantageously, these portal monitoring systems can effectively provide the combined function of a cosmic ray radiography apparatus with passive or active gamma radiation counter to provide a robust detector for nuclear threats. This eliminates the need for two separate instruments.

Cosmic ray tomography is a technique which exploits the multiple Coulomb scattering of highly penetrating cosmic ray-produced muons to perform non-destructive inspection of the material without the use of artificial radiation. The Earth is continuously bombarded by energetic stable particles, mostly protons, coming from deep space. These particles interact with atoms in the upper atmosphere to produce showers of particles that include many short-lived pions which decay producing longer-lived muons. Muons interact with matter primarily through the Coulomb force having no nuclear interaction and radiating much less readily than electrons. They lose energy only slowly through electromagnetic interactions. Consequently, many of the cosmic ray-produced muons arrive at the Earth's surface as highly penetrating charged radiation. The muon flux at sea level is about 1 muon per $cm^2$ per minute.

As a muon moves through material, Coulomb scattering off of the charges of sub-atomic particles perturb its trajectory. The total deflection depends on several material properties, but the dominant effect is the atomic number, Z, of nuclei. The trajectories are more strongly affected by materials that make good gamma ray shielding (such as lead and tungsten for example) and by special nuclear material (SNM), that is, uranium and plutonium, than by materials that make up more ordinary objects such as water, plastic, aluminum and steel. Each muon carries information about the objects that it has penetrated, and by measuring the scattering of multiple muons one can probe the properties of these objects. A material with a high atomic number Z and a high density can be detected and identified when the material is located, inside low-Z and medium-Z matter.

Coulomb scattering from atomic nuclei results in a very large number of small angle deflections of charged particles as the transit the matter. Enrico Fermi found and solved a transport equation that describes this process to a good approximation. The result is a correlated Gaussian distribution function for the displacement and angle change of the trajectory that depends on the density and the atomic charge of the material. The width of the distribution function is proportional to the inverse of the momentum of the particle and the square root of the real density of material measured in radiation lengths. Further background can be found in the reference of K. N Borozdin et al entitled "Surveillance: Radiographic Imaging with Cosmic Ray Muons", published in Nature (2003), 422, 277.

Cosmic ray-produced muons can provide information with no radiation dose above the earth's background and proper detection of such cosmic ray-produced muons can be implemented in a way that is especially sensitive to good shielding materials. A muon detection system can be configured to perform tomography of a target object under inspection based on scattering of muons by the target object. The system can be configured to perform tomography to localize scattering (RC & LS). The tomographic position resolution can be expressed approximately as follows:

$$\Delta x = \theta_{RMS} L \qquad \text{Eq. 1}$$

where:

$\theta_{RMS}$=the root-mean-square (rms) of the scattering angle, and

L=the size of the volume under the detection by the detection apparatus.

For example, for an exemplary rms scattering angle of 0.02 radian and an apparatus size of 200 cm, the tomographic position resolution is 0.02×200 cm=4 cm.

In one approach, the angular resolution is determined by the following equation based on the Poisson statistics:

$$\frac{\Delta\theta}{\theta} = \frac{1}{\sqrt{2N}} \quad \text{Eq. 2}$$

where:

θ=the rms scattering angle,

N=number of cosmic ray-produced muons passing through a region of interest.

For example, the angular resolution for N=100 (corresponding to a 10×10 cm² resolution element after one minute of counting is Δθ=0.07θ.

Referring to the table of FIG. 10, this table illustrates theoretical energy loss rate (dE/dx) and radiation length (X) for various materials. One minute of counting distinguishes a 10 cm cube of iron from a 10 cm cube of lead at 6 standard deviations on the basis of their different values of X.

Tomographic methods, designed to construct an image or model of an object from multiple projections taken from different directions, can be implemented in the cosmic ray system to provide a discrete tomographic reconstruction of the volume of interest based on the data provided by the muons. In some implementations, Monte Carlo simulation techniques can be used to study applications and shorten scanning times. Other stochastic processing methods may also be used in implementing the muon tomographic imaging described in this application.

Figure 4:
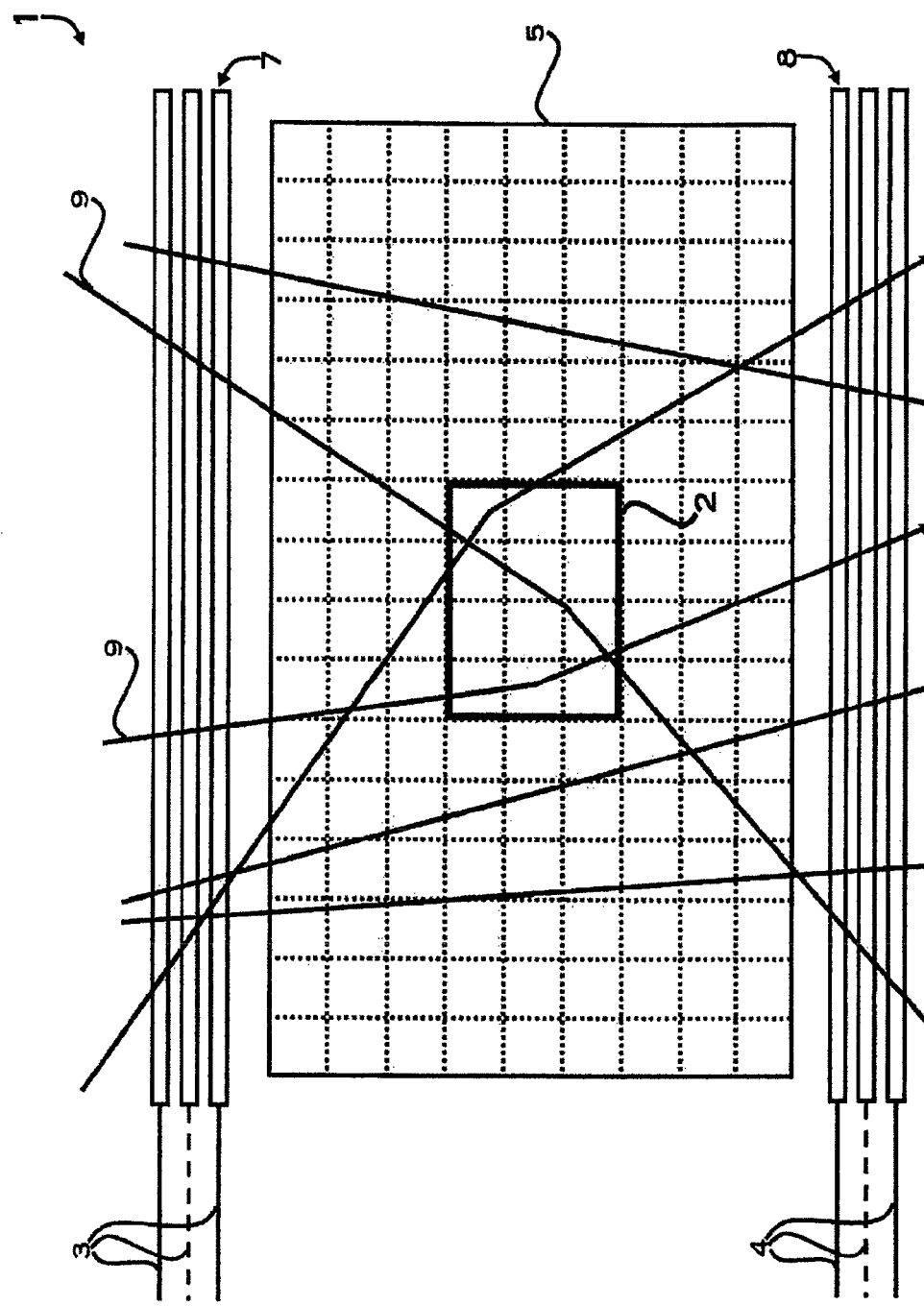
FIG. 4 illustrates a portal monitoring system utilizing cosmic rays to detect an object according to one embodiment.
Figure 5:
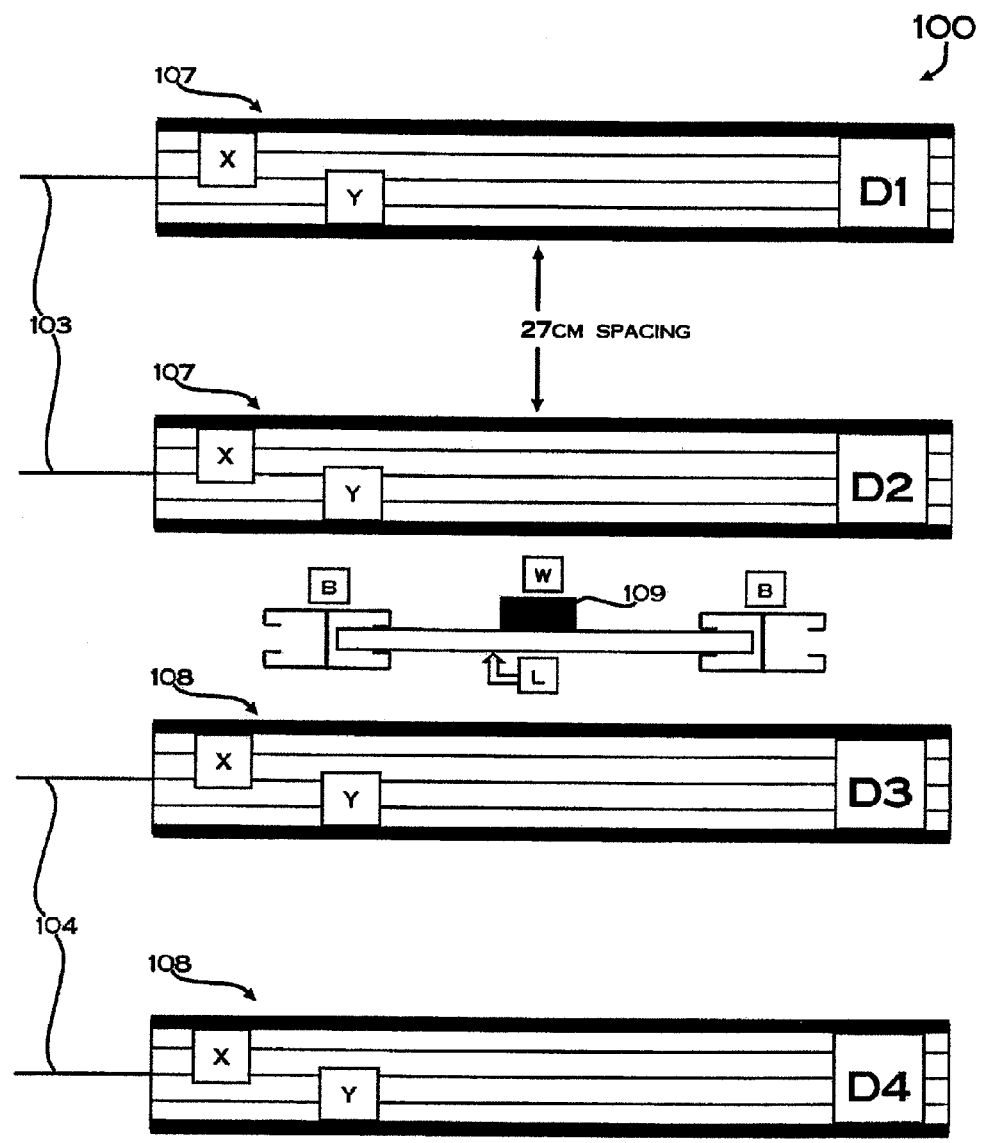
FIG. 5 illustrates a side view of another portal monitoring system utilizing cosmic rays to detect an object according to another embodiment.
Figure 6:
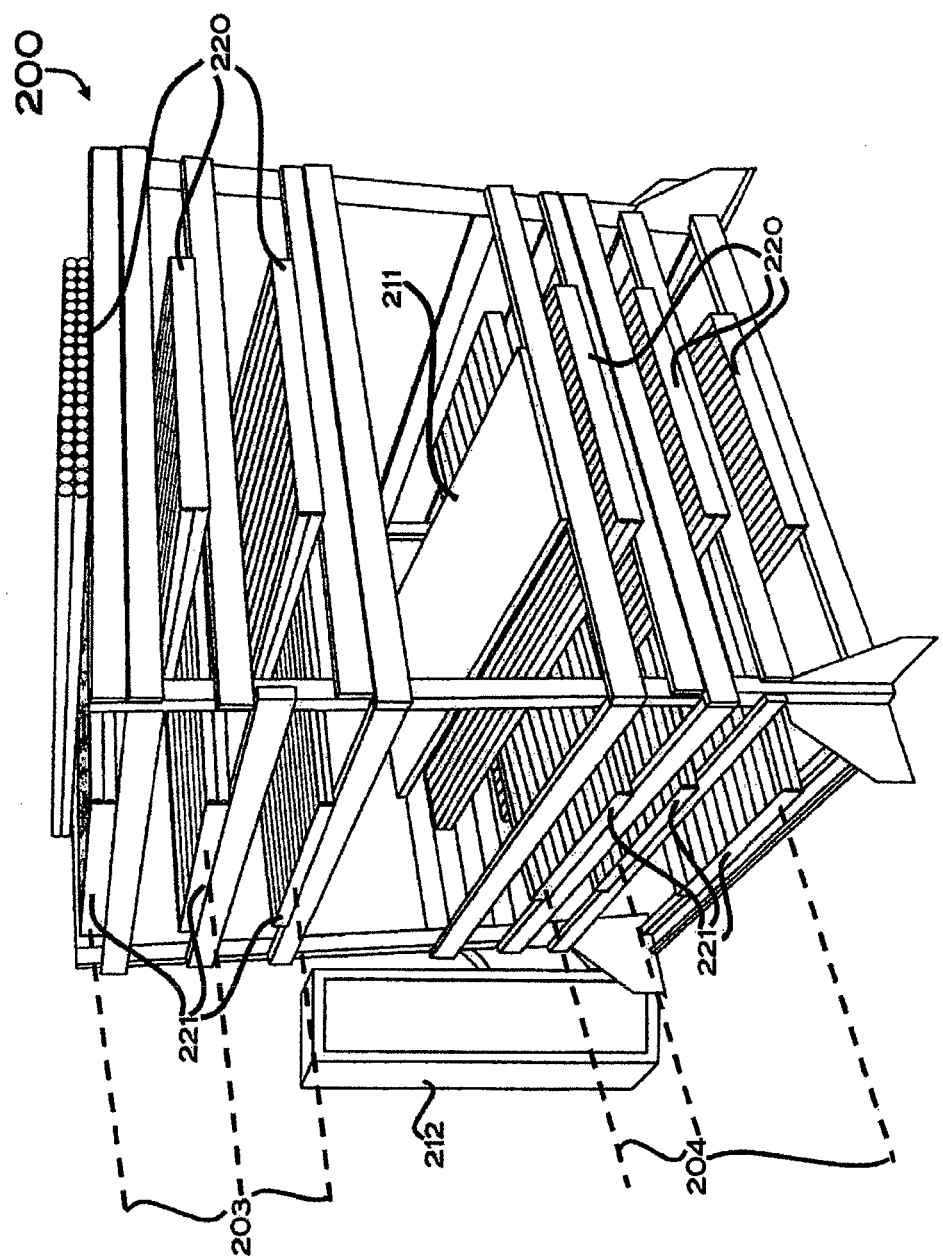
FIG. 6 illustrates a detailed perspective view of a portal monitoring system according to a preferred embodiment.

The cosmic ray radiography function of the particle detection systems of the embodiments can be more readily understood with reference to examples of detection systems adapted to detect cosmic ray-produced charged particles such as those shown in FIGS. 4-6.

Referring initially to FIG. 4, which illustrates a detection system utilizing cosmic ray-produced muons to detect an object, system 1 includes a set of two or more planes 3 of position-sensitive muon detectors 7 arranged above a volume 5 to be imaged for providing the position and angles (i.e., directions in the 3-D space) of incoming muon tracks 9. The muon detectors 7 are configured to measure the position and angles of incoming muon tracks 9 with respect to two different directions, e.g., in two orthogonal coordinates along x and y axes. Muons pass through the volume 5 where the object 2 may be located and are scattered to an extent dependent upon the material 2 occupying the volume through which they pass. Another set of two or more planes 4 of position-sensitive muon detectors 8 are configured to record outgoing muon positions and directions. The drift tubes in detectors 7 and 8 are arranged to allow at least three charged particle positional measurements in a first direction and at least three charged particle positional measurements in a second direction which is different from the first direction and may be orthogonal to the first direction. Side detectors (not shown) may be used to detect more horizontally orientated muon tracks. The scattering angle of each muon is computed from the incoming and outgoing measurements.

A signal processing unit, e.g., a computer, is provided in the system 1 to receive data of measured signals of the incoming muons by the detectors 7 and outgoing muons by the detectors 8. This signal processing unit is configured to analyze the scattering of the muons in the volume 5 based on the measured incoming and outgoing positions and directions of muons to obtain a tomographic profile or the spatial distribution of the scattering density reflecting the scattering strength or radiation length within the volume 5. The obtained tomographic profile or the spatial distribution of the scattering density within the volume 5 can reveal the presence or absence of the object 2 in the volume 5. FIG. 4 shows drift tube detectors 7 and 8 are located on top and bottom sides of the volume 5. In some implementations, additional drift tube detectors can be implemented on sides of the volume 5 to form a box or four sided structure into which a package, a vehicle or cargo container can enter for scanning by the system.

The processing of measurements for cosmic ray-produced muons in a volume under inspection (e.g., a package, a container or a vehicle) by the processing unit for the system 1 in FIG. 4, and other systems described in this application can include reconstructing the trajectory of a charged particle such as a muon through the volume 5, measuring the momentum of an incoming muon based on signals from the detectors 7, measuring the momentum of an outgoing muon based on signals from the detectors 8, and determining the spatial distribution of the scattering density of the volume 5. These and other processing results can be used to construct the tomographic profile and measure various properties of the volume 5.

For example, the reconstruction of the trajectory of a charged particle passing through a detector having a set of drift cells can include (a) obtaining hit signals representing identifiers of drift cells hit by charged particles and corresponding hit times; (b) grouping in-time drift cell hits identified as being associated with a track of a particular charged particle passing through said detector; (c) initially estimating a time zero value for a moment of time at which said particular charged particle hits a drift cell; (d) determining drift radii based on estimates of the time zero values, drift time conversion data and the time of the hit; (e) fitting linear tracks to drift radii corresponding to a particular time zero value; and (f) searching and selecting a time-zero value associated with the best of the track fits performed for a particular charged particle and computing error in time-zero and tracking parameter. Such reconstruction of the track based on the time zero fit provides a reconstructed linear trajectory of the charged particle passing through the charged particle detector without having to use fast detectors (such as photomultiplier tubes with scintillator paddles) or some other fast detector which detects the passage of the muon through the apparatus to the nearest few nanoseconds to provide the time-zero.

Also for example, the processing for measuring the momentum of an incoming or outgoing muon based on signals from the detectors can include, for example, (a) configuring a plurality of position sensitive detectors to scatter a charged particle passing therethrough; (b) measuring the scattering of a charged particle in the position sensitive detectors, wherein measuring the scattering comprises obtaining at least three positional measurements of the scattering charged particle; (c) determining at least one trajectory of the charged particle from the positional measurements; and (d) determining at least one momentum measurement of the charged particle from the at least one trajectory. This technique can be used to determine the momentum of the charged particle based on the trajectory of the charged particle which is determined from the scattering of the charged particle in the position sensitive detectors themselves without the use of additional metal plates in the detector.

Also for example, the spatial distribution of the scattering density of the volume can be determined from charged particle tomographic data by: (a) obtaining predetermined charged particle tomography data corresponding to scattering angles and estimated momentum of charged particles passing through object volume; (b) providing the probability distribution of charged particle scattering for use in an expectation maximization (ML/EM) algorithm, the probability distribution being based on a statistical multiple scattering model; (c)

determining substantially maximum likelihood estimate of object volume density using the expectation maximization (ML/EM) algorithm; and (d) outputting reconstructed object volume scattering density. The reconstructed object volume scattering density can be used to identify the presence and/or type of object occupying the volume of interest from the reconstructed volume density profile. Various applications include cosmic ray-produced muon tomography for various homeland security inspection applications in which vehicles or cargo can be scanned by a muon tracker.

The tomographic processing part of the signal processing unit may be implemented in a computer at the same location as the detectors 7 and 8. Alternatively, the tomographic processing part of the signal processing unit may be implemented in a remote computer that is connected on a computer network such as a private network or a public network such as the Internet.

Thus, multiple scattering of cosmic ray-produced muons can be used to selectively detect high z-material in a background of normal cargo. Advantageously, this technique is passive, does not deliver any radiation dose above background, and is selective of high-z dense materials.

Referring to FIG. 5, which illustrates a side view of another detection system utilizing cosmic rays to detect an object, the system 100 has two planes 103 of muon detectors 107 located above the sample 109 and two planes 104 of muon detectors 108 located below the sample 109. In the system 100 the planes of muon detectors are separated by 27 cm spacings.

FIG. 6 illustrates a detailed perspective view of another charged particle detector 200 in which position sensitive detectors 203 are arranged above the sample holder plane 211 and position sensitive detectors 203 are arranged below the sample holder plane 211. Each set of position sensitive detectors comprises a first double-layer 220 of drift tubes 204 arranged in the X direction and a second double-layer 221 of drift tubes 204 arranged in the Y direction. In each of the layers 220, 221, the drift tubes 204 are arranged in two rows, offset by half a tube diameter from each other.

Drift tube modules 204 are operable to detect both cosmic ray-produced muons and gamma rays. In the system of FIG. 6, the drift tube modules are 12 foot long aluminum drift tubes which are configured to measure the position and angle of incoming and outgoing muon tracks in X and Y coordinate directions. The aluminum in the detectors provides a considerable amount of mass in which gamma rays and energetic electrons are absorbed or scattered. The energetic electrons produced in these processes are detected locally in the drift tubes in the same way that more energetic cosmic rays are detected.

The tubes can be arranged in different ways. For example, the layers need not have to be 90 degrees from one another, but can be smaller non-zero angles. Also by way of example, the top layer could be at 0 degrees, middle layer at 45 degrees from the first, and a third layer 90 degrees from the first. This would allow resolution of multiple tracks that occur at the same instance of time.

Also, other position sensitive detector arrangements capable of scattering the charged particle passing therethrough and providing a total of at least three individual positional measurements can be adopted instead of the arrangement of detectors of FIG. 6. At least 3 position measurements are required so as to enable a line fit with a free parameter from which one can track the particle.

One example of the data acquisition electronics 212, operably coupled to the drift tubes, will now be described. Drift tubes of the detector system 200 of FIG. 6 are connected to respective electronic amplifiers (not shown) which increase the voltage of the deposited signal (associated with a cosmic ray-produced muon passing through a drift tube). For each drift channel, the amplified signal is turned into a digital signal with a piece of electronics called a discriminator (on if there is a hit, off if no hit), which preserves the precise time of the hit. This combination of amplifier and discriminator is the "front-end" electronics. The time and channel number that the digital signal is registered to the nearest nanosecond by the time-to-digital-converters (TDCs) mentioned above. Each drift tube has its own front-end electronics and TDC.

The front-end electronics is built using hardware composed of off-the-shelf (OTS) parts. The TDC is OTS, and the units are built by Caen corporation in Italy. Each TDC unit (CAEN 767B) has the capability of 128 input channels (drift tubes in our case), and will store the time of the hit digitally. These units have a buffer which can hold about 32,000 hits. The TDCs are read-out about 5 times per second with a custom data-acquisition system (DAQ). The TDCs sit in a Versa Module Eurocard VME crate with a SIS 1100 controller, made by Struck Innovative Systeme GmbH (SIS), which provides the computer interface. The DAQ runs on a personal computer, with an optical cable to interface with the SIS 1100 to command the TDCs for the data transfer. Once the hit times and channel numbers are read out into the memory of the PC, the raw data is stored on hard drive, but the data is also processed to identify the cosmic ray events. The track data, and pertinent diagnostic data are also stored on the hard drive. The processing of measurements for cosmic ray-produced muons in a volume under inspection (e.g., a package, a container or a vehicle) by the data acquisition unit of the system of FIG. 6, or other signal processing unit linked thereto, can be similar to those explained above for the system of FIG. 4. For example, processing measurements may be reconstructing the trajectory of a muon through the volume, measuring the momentum of an incoming muon based on signals from the detectors, measuring the momentum of an outgoing muon based on signals from the detectors, and determining the spatial distribution of the scattering density of the volume.

Advantageously, system 200 can selectively detect high density shielding of radioactive material occupying the volume from multiple scattering of the cosmic ray-produced muons whilst also counting gamma rays emitted from the radioactive material. In addition to detecting high density materials, such as lead, gold, tungsten, uranium and plutonium, the system can be employed to detect medium density materials, such as steel, iron and copper, and also low density materials, such as water, plastic, concrete and aluminum, albeit with a somewhat lower accuracy than for high density materials.

Figure 7:
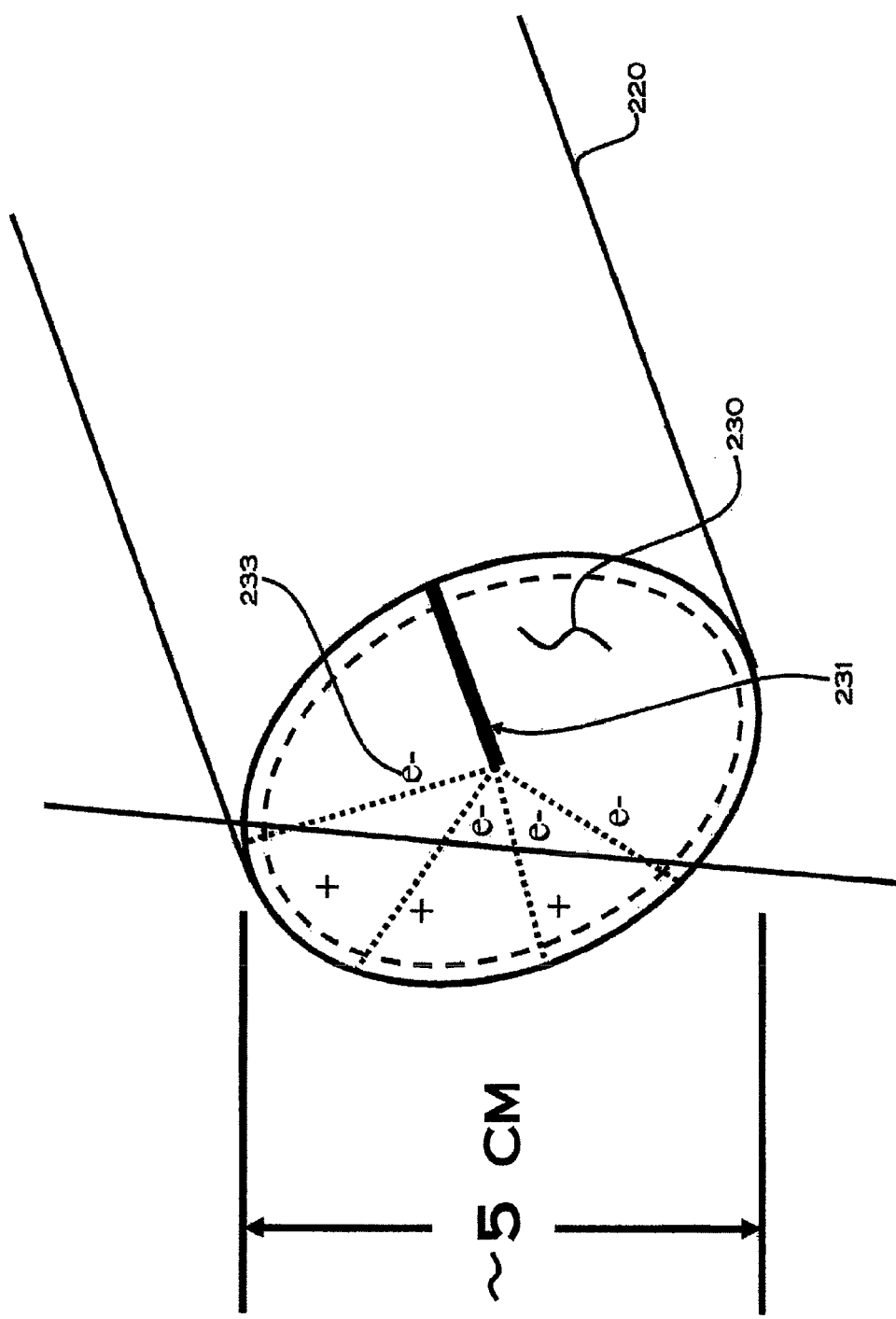
FIG. 7 illustrates a cross-sectional view of part of a drift tube module configured to detect cosmic ray charged particles and gamma rays according to one embodiment.

A cross-sectional view of part of a typical drift tube module 204 is illustrated in FIG. 7. The drift tube module in this particular example is cylindrical and filled with a detector gas such as Argon-Isobutane 230 to enable detection of the cosmic ray-produced charged particles, such as muons. The system is configured to apply a positive high voltage of about +2-3 kV to a central anode wire 231 extending along the length of the cylindrical tube with the tube at ground so that a high-voltage static field is also present. When the charged particle interacts with gas atoms, many electrons 233 are liberated from those atoms along the charged particle's straight line path through a chord of the tube. The static field causes the "string" of electrons to drift toward the positively charged anode wire which is read-out electronically with TDCS (time-to-digital converters) of the data acquisition electronics 212.

Whilst in the drift tube of the illustrative embodiment of FIG. 7, the detector gas is Argon-Isobutane 230, other operating gas mixtures may be Argon/carbon dioxide or Argon/isobutane/carbon dioxide and can include hydrocarbons such as methane, propane, pentane and the like. An example of an operating gas mixture is 10% methane, 90% argon. Furthermore, non-flammable gas mixtures such as Argon-carbon-dioxide-tetrafluoromethane ($CF_4$) may alternatively be employed as the operating gas. Also, ethane or other gases may be adopted in the gas mixtures. For example, a mixture of 5% of ethane, 45% of CF4 and 50% of Argon is a suitable non-flammable operating gas. Inert gases other than Argon can be used in the gas mixture.

Also, whilst the drift tube of FIG. 7 is manufactured from aluminum, other materials such as carbon composite with internal conductive coatings can be adopted instead of aluminum. The drift tubes need not have circular cross-sections. For example, the drift tubes may be constructed from aluminum extrusions with multiple, non-circular cross-sections.

Alternatively, drift cells other than drift tubes can be adopted such as for example triangular shaped drift cells.

Figure 8:
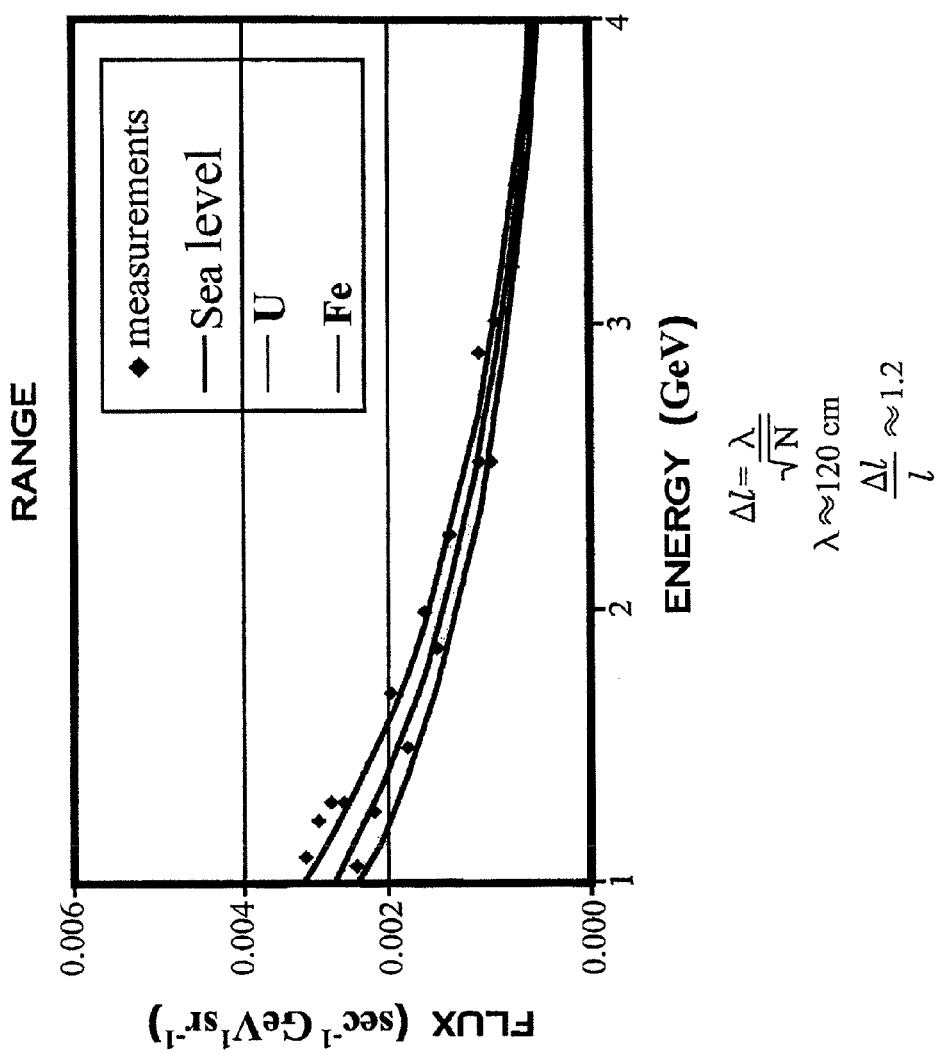
FIGS. 8 and 9 respectively illustrate typical experimental range data and multiple coulomb scattering theoretical results of measuring 1000 $cm^2$ of uranium for 1 minute with a cosmic ray system.
Figure 9:
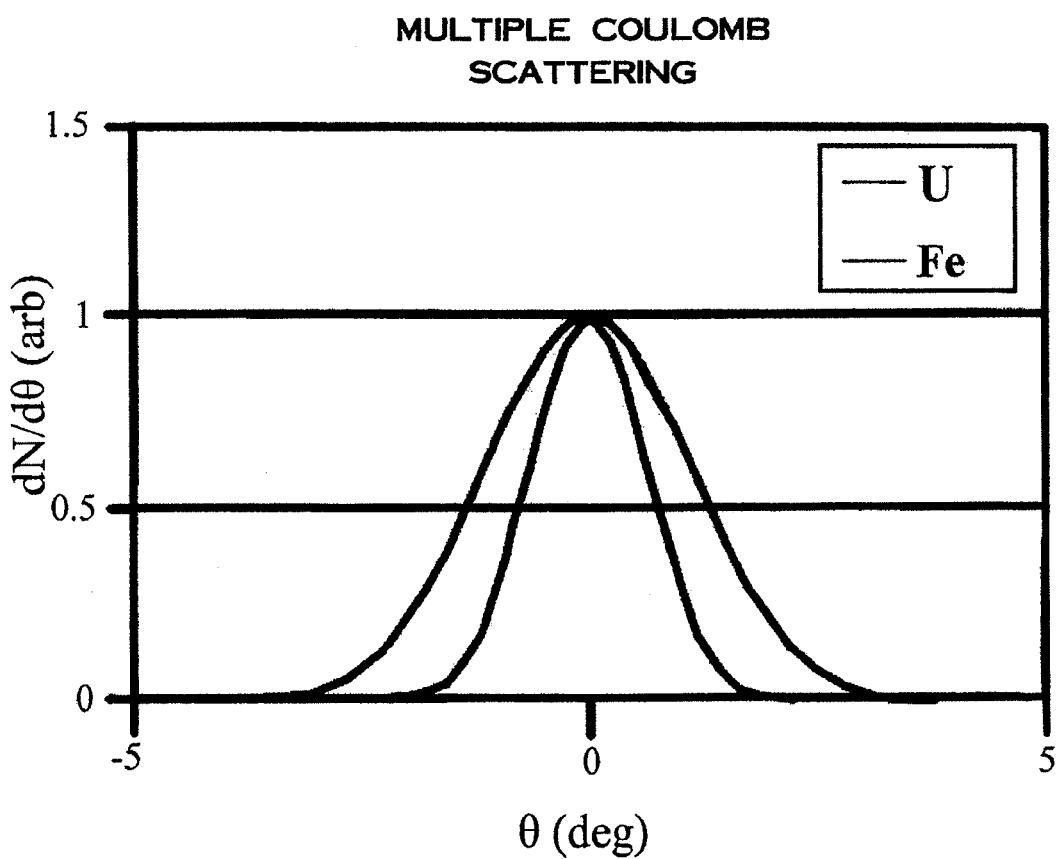

FIGS. 8 and 9 respectively illustrate exemplary experimental range data and multiple Coulomb scattering theoretical results of measuring 1000 $cm^3$ of uranium for 1 minute with a cosmic ray-produced muon detection system. These measurements and computations demonstrate that charged particle (muon) tomography is much more sensitive than the range radiography previously employed in searches for hidden chambers in an Egyptian pyramid and measurement of geological overburden.

Figure 11:
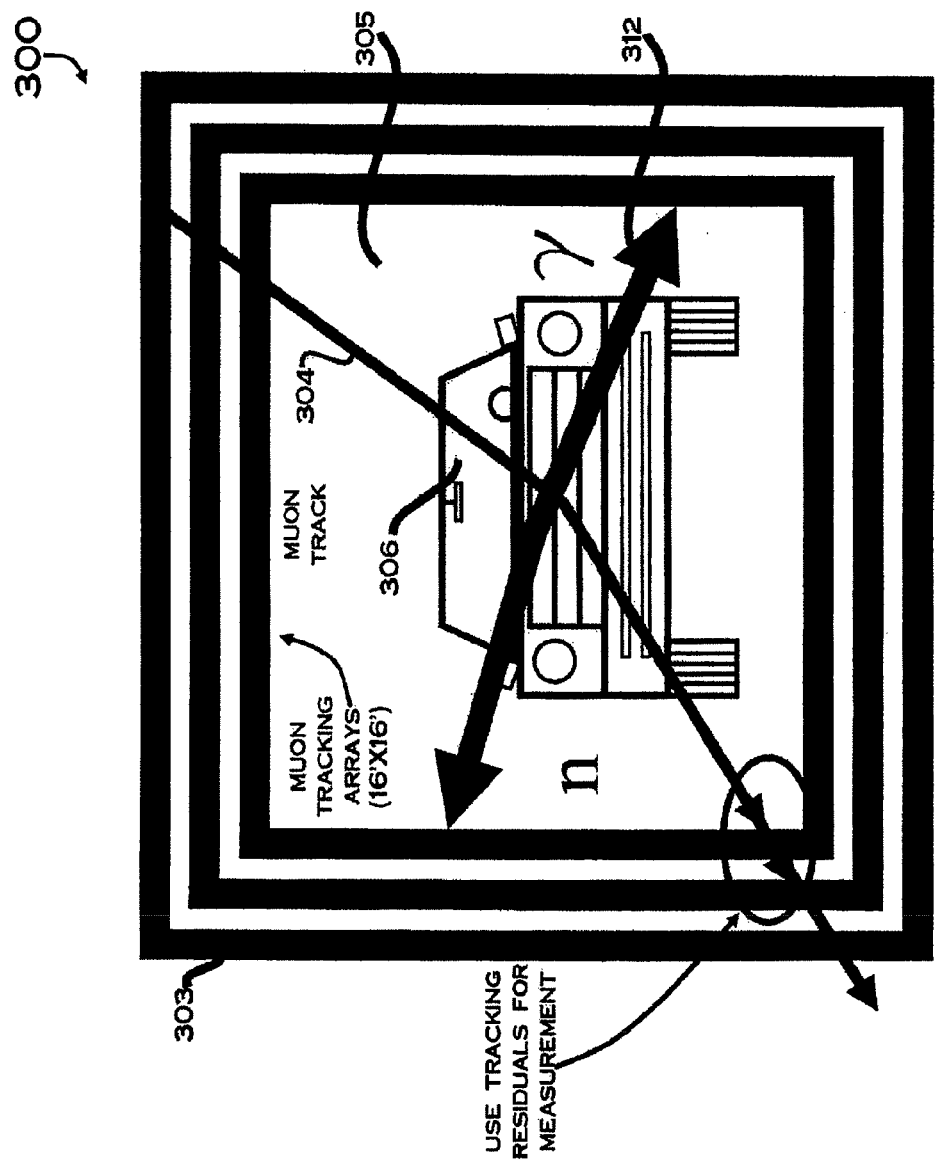
FIGS. 11 and 12 illustrate portal monitoring systems adapted and arranged to monitor cargo in vehicles and containers according to alternative embodiments.

FIG. 11 illustrates a particle detection system 300 adapted and arranged to monitor cargo in vehicles and containers at ports and border crossings according to one embodiment. As will be explained in more detail below, the particle detection system 300 uses a muon tomography system with a plurality of detector drift tubes 303 configured to track cosmic ray-produced muons 304 scattered by the cargo or contents of a vehicle 306 occupying the volume 306 and configured to concurrently detect any neutrons 314 emitted from the vehicle contents. The system 300 can be employed for inspecting occupied vehicles at border crossings for nuclear threat objects which might range from fully assembled nuclear weapons to small quantities of highly shielded nuclear materials. The system 300 can be used to pass innocent vehicles in less than 30 seconds, detect several Kgs of highly enriched uranium (HEU) in less than 60 seconds (shielded or unshielded) and detect plutonium or HEU nuclear devices in less than 60 seconds (shielded or unshielded).

Advantageously, using the drift tubes 303 to both passively count gamma radiation 312 emitted from the vehicle 306 and track the scattered cosmic ray-produced charged particles 304 enables the system to perform passive scanning of occupied passenger vehicles with short scanning times and no dose radiation.

A method of operating the particle detection system (such as a portal monitoring system) 300 of FIG. 11 according to one embodiment involves detecting with the drift tubes 303 incoming and outgoing cosmic ray-produced charged particles 304 together with any gamma rays 312. The multiple scattering of the charged particles are then computed to selectively detect a material, particularly high density material, occupying the volume 305. Gamma rays 312 emitted from the volume can be counted by the data acquisition electronics to detect whether any radioactive source is occupying the volume 305.

In an alternative embodiment, a portal monitoring system (not shown) is provided which is identical to that of the portal monitoring system 300 of FIG. 11 with the exception that the system also includes a gamma ray or neutron source within the apparatus to enable active rather than only passive interrogation of the vehicle and thereby provide a detectable increase in the gamma ray counting rate.

Figure 12:
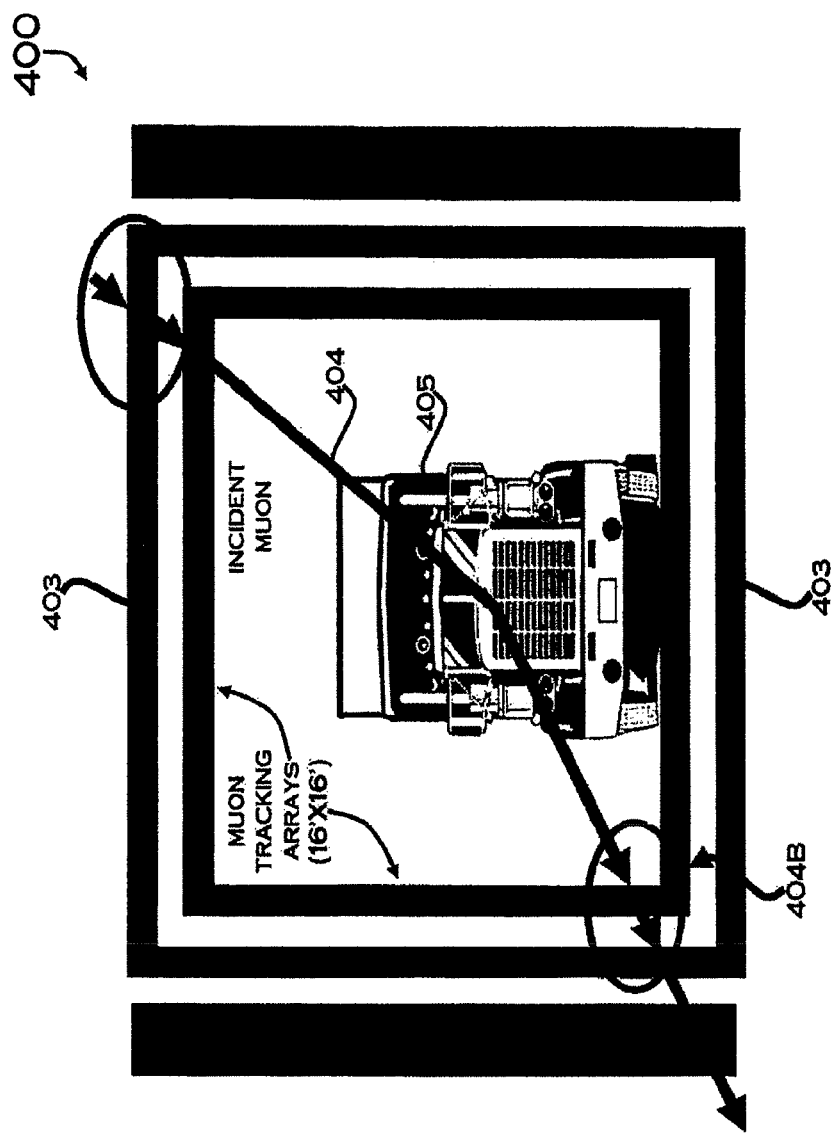

A particle detection system (e.g., a portal monitoring system) according to another alternative embodiment is illustrated in FIG. 12. System 400 is similar to the system 300 of FIG. 11 in that it is configured to both passively count gamma radiation emitted from the vehicle and track the scattered cosmic ray-produced charged particles 404. The drift tube detectors arrays 403 are 16 foot long to enable interrogation of a truck 405 but may be other lengths dependent on the object being scanned. In order to obtain major gains in rate, the solid angle can be increased by filling out the drift tube detectors 403. Furthermore, the system is configured to use tracking residuals 404B for momentum measurements.

In another alternative embodiment, a portal monitoring system which is identical to the system 300 of FIG. 11, has drift tubes which are sealed advantageously further to decrease cost and complexity of the system by eliminating the need for a gas handling system.

The aforementioned illustrative embodiments demonstrate that the combination of cosmic ray radiography with passive or active counting therefore provides a robust detector for nuclear threats. Conventional radiography alone is defeated by packaging nuclear material in packages too small to be resolved by the radiography. Passive counting can be defeated by shielding the material with high-z material. The shielding makes the threats move visible radiographically and dispersing the material in many cases enhances the passive signature. Combining these techniques allows one to determine if a given vehicle is free of threats by measuring the absence of a potential shielded package and the absence of a radiation signature.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only.

Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A particle detection system, comprising:
   a first set of position sensitive charged particle detectors located on a first side of an object holding area to measure positions and directions of incident charged particles towards the object holding area;
   a second set of position sensitive charged particle detectors located on a second side of the object holding area opposite to the first side to measure positions and directions of outgoing charged particles exiting the object holding area;
   means for processing scattering of the charged particles in the materials within the object holding area based on the measured incoming and outgoing positions and directions of charged particles to obtain a tomographic profile or the spatial distribution of scattering centers within the object holding area, means for reconstructing a trajectory of a charged particle through the object holding area;

means for measuring a momentum of an incoming charged particle based on signals from the first set of position sensitive charged particle detectors;

means for measuring a momentum of an outgoing charged particle based on signals from the second set of position sensitive charged particle detectors;

means for obtaining a spatial distribution of a scattering density of the object holding area, means for determining spatial distribution of the scattering density of the object holding area to obtain predetermined charged particle tomography data corresponding to scattering angles and estimated momentum of charged particles passing through the object holding area;

means for producing a probability distribution of charged particle scattering for use in an expectation maximization algorithm based on a statistical multiple scattering model; and means for determining a substantially maximum likelihood estimate of the scattering density of the object holding area using the expectation maximization algorithm, wherein the first set of position sensitive charged particle detectors includes a first double-layer of drift tubes arranged in an X direction and a second double-layer of drift tubes arranged in a Y direction.

2. The system as in claim 1, wherein the drift tubes are arranged to allow at least three charged particle positional measurements in a first direction and at least three charged particle positional measurements in a second direction different from the first direction.

3. The system as in claim 1, wherein the drift tubes are adapted and arranged on surrounding sides of the object holding area to form a box or four sided structure.

4. The system as in claim 1, further comprising:
means for using the scattering density to identify either or both of presence and type of an object in the object holding area.

5. The system as in claim 1, wherein each position sensitive charged particle detector is structured to detect both cosmic ray-produced muons and gamma rays.

6. The system as in claim 1, wherein each drift tube is filled with a gaseous medium.

7. The system as in claim 6, wherein the second set of position sensitive charged particle detectors includes a plurality of layers of drift tubes where at least two layers of drift tubes have different orientations.

8. The system as in claim 1, wherein
the drift tubes in the first double-layer and the second double-layer are arranged in two rows, offset by half a tube diameter from each other.

9. A system for sensing a presence or absence of a material in a target object, comprising:

means for holding the target object to expose the target object to incident charged particles;

a first set of position sensitive charged particle detectors located on a first side of the target object to measure positions and directions of incident charged particles towards the target object before reaching the target object and to produce first detector signals containing information of the incoming charged particles;

a second set of position sensitive charged particle detectors located on a second side of the target object opposite to the first side to measure positions and directions of outgoing charged particles exiting the target object and to produce second detector signals containing information of the outgoing charged particles;

means for analyzing scattering of the charged particles in the target object based on the positions and directions of the incoming and outgoing charged particles to obtain a tomographic profile or the spatial distribution of scattering centers within the target object;

means for processing the tomographic profile or the spatial distribution of scattering centers to determine a presence or absence of a material in the target object; and means for obtaining an angle and momentum of each charged particle passing through the target object to provide a probability distribution of charged particle scattering;

wherein the first set of position sensitive charged particle detectors includes a first double-layer of drift tubes arranged in an X direction and a second double-layer of drift tubes arranged in a Y direction.

10. The system as in claim 9, wherein the target object is exposed to muons in cosmic rays and the outgoing charged particles include scattered muons.

11. The system as in claim 10, wherein the outgoing charged particles include the scattered muons and gamma rays coming out of the target object, and the second set of positive sensitive detectors are responsive to both scattered muons and gamma rays from the target object.

12. The system as in claim 9, comprising:
means for determining a type of the material present in the target object after a material is determined to be present in the target object.

13. The system as in claim 12, wherein the type is determined based on atomic numbers of materials.

14. The system of claim 9, wherein:
the drift tubes in the first double-layer and the second double-layer are arranged in two rows, offset by half a tube diameter from each other.

* * * * *